Figure 1:
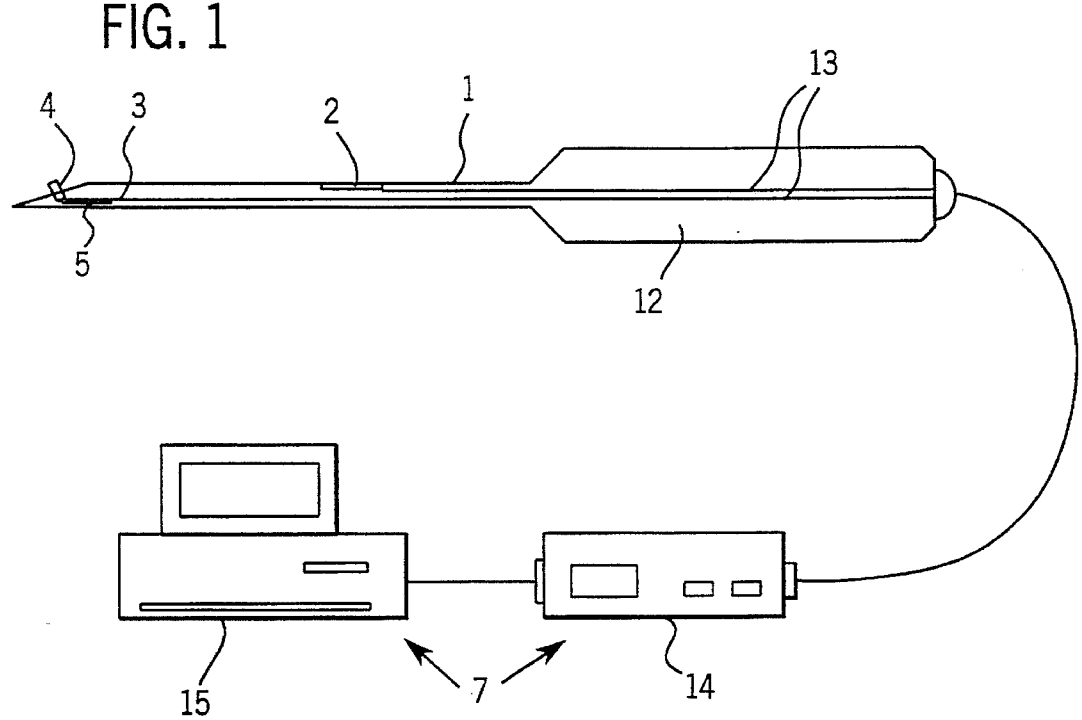

United States Patent [19]
Kiviranta et al.

[11] Patent Number: 5,494,045
[45] Date of Patent: Feb. 27, 1996

[54] MEASURING DEVICE AND MEASURING PROCEDURE FOR ASSESSING THE STIFFNESS OF RIGID TISSUE

[76] Inventors: Ilkka Kiviranta, Taivallahdentie 7, FIN-70620 Kuopio; Jukka Jurvelin, Kuopion Yliopisto Anatomian laitos, Box 1627, FIN-70211 Kuopio, both of Finland

[21] Appl. No.: 240,642

[22] PCT Filed: Jul. 28, 1992

[86] PCT No.: PCT/FI92/00220

§ 371 Date: Apr. 12, 1994

§ 102(e) Date: Apr. 12, 1994

[87] PCT Pub. No.: WO93/02619

PCT Pub. Date: Feb. 18, 1993

[30]  Foreign Application Priority Data

Aug. 1, 1991 [FI] Finland ................... 913673

[51] Int. Cl.⁶ .................................. A61B 5/10
[52] U.S. Cl. .................................. 128/774
[58] Field of Search .................. 128/744, 774; 73/78, 81

[56]     References Cited

U.S. PATENT DOCUMENTS

| | | | |
|---|---|---|---|
| 3,133,355 | 5/1964 | Gordon | 128/774 |
| 4,132,224 | 1/1979 | Randolph. | |
| 4,159,640 | 7/1979 | Leveque et al. | 128/774 |
| 4,364,399 | 12/1982 | Dashefsky | 128/774 |
| 4,365,638 | 12/1982 | Lévêque et al. | 128/774 |
| 4,503,865 | 3/1985 | Shishido | 128/774 |
| 4,928,707 | 5/1990 | Schiffman et al. | 73/81 |
| 4,964,412 | 10/1990 | Kelly | 128/744 |
| 5,224,469 | 7/1993 | Mocny | 128/774 |

OTHER PUBLICATIONS

International Search Report PCT/FI92/00220 dated Nov. 13, 1992.

*Primary Examiner*—Max Hindenburg
*Attorney, Agent, or Firm*—Andrus, Sceales, Starke & Sawall

[57]     ABSTRACT

A device for measuring the stiffness of rigid tissue, such as cartilage. The device comprises an elongated, rigid body (1) and a first transducer (2) for measuring the force acting on the body. The body has an abutment face (6) for pressing against the tissue that is being measured, which face surrounds a measuring arm (3) having a protruding measuring pin (4). A second transducer (5) is provided for measuring the force acting from the tissue under measurement, through the measuring pin, and on the measuring arm. A signal processor (7) is included for processing the signals from the transducers.

10 Claims, 1 Drawing Sheet

MEASURING DEVICE AND MEASURING PROCEDURE FOR ASSESSING THE STIFFNESS OF RIGID TISSUE

The present invention concerns a stiffness measuring device and a measuring procedure for assessing the stiffness of rigid tissue.

In particular, the invention deals with a stiffness measuring device for use in assessing the stiffness of articular cartilage, and in the disclosure following below articular cartilage is exclusively considered as tissue that is being measured. However, the stiffness measuring device of the invention is not restricted to be used only in measuring articular cartilage stiffness: it can be applied in like manner in assessing the stiffness of any other equivalent tissues.

Articular cartilage is differentiated connective tissue containing no blood vessels, lymphatic vessels or nerves. Articular cartilage is stiffest among the soft tissues of the body, yet clearly softer than bone. The articular cartilage differs in thickness in different joints, from a few micrometers up to several mm. The cartilage thickness may also be different in different parts of the articular surfaces. The two main tasks of the articular cartilage are: to reduce the load on the underlying bone, and to act towards low friction in the joint.

Chondromalacia is a degenerative disease of the articular cartilage, its causative agent being as yet unknown. It is however highly common, in that as many as one-third of the adult population have been estimated to have changes in their patellar chondral surface. Nearly all symptomatic patients present softened patellar cartilage although the cartilage may appear normal macroscopically. Softening is in fact the first observable change in the chondral surface caused by chondromalacia. At a later stage the chondral surface becomes uneven and frayed. Diagnosis of chondromalacia in its initial stage is important because the changes are irreversible once fraying has taken place.

At present, mechanical characteristics of articular cartilage are mostly measured using material testing apparatus. Such bulky and heavy apparatus is not transportable; it is therefore only applicable in laboratory conditions for studies on specimens.

The simplest method employed in operating theatre conditions for assessment of articular cartilage stiffness is pressing down on the chondral surface with a metallic instrument in connection with surgery. The results of such measurements are however highly subjective and variable.

So far only two measuring instruments have been proposed for peroperative use. One is the cartilage elastometer, its use requiring opening of the knee joint, whereby its use is cumbersome. The other is a measuring instrument which can be used arthroscopically, i.e., in connection with optical viewing of the joint. In this instrument a pressure transducer is employed which has a pressure-sensitive membrane on one end. The transducer is mounted in a curved steel tube in such a way that the pressure-sensitive end of the transducer remains slightly inside the end of the tube. On the end of the tube is attached a sphere made of elastic material, its surface abutting tightly on the transducer membrane and thereby transmitting a pressure signal. The other side of the sphere is located outside the metal tube.

In the measurement the end of the instrument is pressed against the cartilage until the metallic end of the socket precludes further pressing. The elastic sphere on the tip of the measuring instrument is flattened against the cartilage; the higher the stiffness of the cartilage, the greater the flattening of the sphere. At the same time, it transmits to the pressure transducer the force produced by the cartilage. The relationship between cartilage stiffness and tension reading is however not linear. In principle this pressure transducer enables forces produced by the cartilage to be measured, but mathematical modelling of this measurement is difficult because the deformation caused in the cartilage by the transducer is not known. It is also unclear what effect the cartilage thickness has on the result of measurement.

The object of the invention is to eliminate the drawbacks mentioned. Specifically, the object of the invention is to disclose a novel stiffness measuring instrument, and a procedure, for measuring the stiffness of soft tissue, e.g. of articular cartilage, in a manner affording objective and accurate results of measurement and enabling the measurement to be performed rapidly and simply in connection with arthroscopy.

Regarding the characteristic features of the invention, reference is made to the Claims section.

The instrument of the invention for measuring the stiffness of rigid tissue comprises an elongated rigid body having an abutment surface to be pressed in the measurement against the surface of the tissue to be studied. The instrument further comprises a measuring arm resting against said body and carrying a protruding measuring knob or other equivalent projection, wart or pin of comparatively small size. The measuring arm also carries a transducer for measuring the stress acting thereon from the tissue under measurement, transmited by the measuring knob. The stiffness measuring instrument moreover comprises means for receiving the signals from said transducer and processing them to such form as is desired.

Advantageously, the body also includes a transducer which measures the stress imposed on the body. Likewise, the apparatus entity comprises means with which the signals from both transducers are processed and on the basis of said signals an output characterizing the tissue under examination is produced.

Advantageously, strain gauges are used for transducers, while other kinds of transducer structures separately known in themselves and employed in various connections can equally be contemplated.

In an advantageous embodiment of the invention, the measuring arm is substantially in its entirety surrounded by a protective socket, this socket constituting an abutment face which in the measurement rests against the surface of the tissue that is being measured. In that case, the protective socket is provided with an aperture through which the measuring pin protrudes outside the outer surface of the protective socket. The aperture is advantageously so dimensioned that a clear gap is left between the margins of the aperture and the measuring pin, whereby the protective socket will not interfere with the movements of the measuring pin nor thus affect the results of measurement.

Advantageously, the measuring pin projects from the aperture in the protective socket a distance between 0.1 and 1.0 mm, possibly 0.2 to 0.5 mm, e.g. 0.36 mm, outside the abutment face.

The abutment face of the body is advantageously substantially straight in the direction longitudinal to the body, and it may run parallel with the elongated body or at an angle thereagainst so that its inclination against the elongated body is 0° to 45°, advantageously 10° to 30°, e.g. about 20°. The device is then easy to push up against the articular cartilage surfaces in arthroscopic measurements.

In an embodiment of the invention, when the measuring arm is located within a protective socket, the protective socket comprises at least one, advantageously two, cleaning apertures which enable the space between protective socket and measuring arm to be cleaned and the measuring device to be scrupulously disinfected, whenever needed.

In another embodiment of the invention, the protective socket has no cleaning apertures, instead of which the free space between the measuring pin and the protective socket is sealed with a suitable, resilient and sealing compound which efficiently precludes entry of impurities into the protective socket, whereas free movement of the measuring pin relative to the protective socket is not impeded.

Advantageously, the transducers implemented with strain gauges, on the measuring arm as well as the body, are implemented with strain gauge pairs so that any phenomena due to thermal expansion of the metals will be eliminated. This is, for instance, implemented in the way that the strain gauges are placed on opposite sides both on the measuring arm and on the body and, furthermore, with such placement relative to the measuring pin and to the abutment face that in the event of a load acting on the transducer one strain gauge of the transducer will respond to compression and the other to distension.

In the procedure of the invention for measuring the stiffness of rigid tissue, a substantially punctiform load entering to a constant depth is directed on the tissue under measurement, this load compressing the tissue without causing damage. The force from the tissue counteracting the compression is measured in order to determine the stiffness of the tissue. A substantially punctiform load is in this case understood to be a load having an active area of diameter on the order of 1 mm. It is thus understood that no point-like spike is used to produce the load, which would penetrate the tissue causing damage to it: the load action surface is a suitable, small straight or curved surface which compacts the tissue ahead of itself, causing no damage to the tissue.

Advantageously, in the procedure of the invention, a planar load is moreover directed on the tissue under measurement, the stiffness of the tissue being determined from the planar and punctiform loads in combination, where the planar load represents the force with which the measuring device is pressed against the tissue and the punctiform load represents the force with which the tissue under measurement resists the load that is being applied.

The advantage of the invention over prior techniques is that it enables the stiffness of suitable tissues, such as articular cartilages, to be measured accurately and objectively so that from the results of measurement the state of the measured tissue is ascertained with ease.

Figure 2:
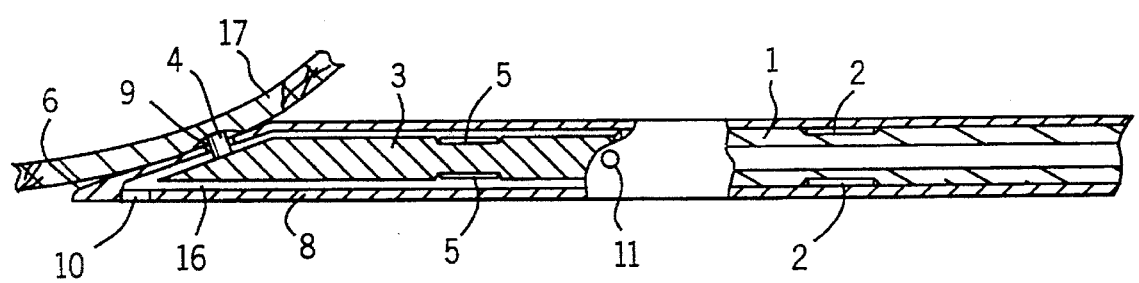

In the following the invention is described in detail with reference to the attached drawings, wherein FIG. 1 presents, schematically, a stiffness measuring device according to the invention with its different parts, and FIG. 2 presents the structural design of the stiffness measuring device of FIG. 1, partly sectioned.

The stiffness measuring device according to the invention depicted in FIG. 1 comprises a straight, elongated and rigid body 1, carrying a strain gauge transducer 2 disposed to measure loads acting on the body. The body has on one end a thickened portion 12 constituting a handle by which the device is held when it is used. The other end of the body, its tip, contains a measuring arm 3 on which a measuring pin 4 rests, protruding out from the body. The measuring arm 3 is also provided with a transducer 5 which measures the force acting on the measuring arm through the measuring pin.

Both transducers 2 and 5 are connected to measurement processing means 7, consisting of an electronics unit 14 and of output apparatus 15, by the aid of which the signals that are measured can be processed and registered in such form as is desired.

In the manner shown in FIG. 2, the tip part of the stiffness measuring device of the invention comprises a rigid tubular body 1 in extension of which a rod-like measuring arm 3 has been rigidly attached thereto. The body as well as the measuring arm are substantially circular in cross section.

Encircling the body 1 as well as the measuring arm 3 has been provided a unitary tubular protective socket 8, extending over the measuring arm 3 and covering the measuring arm within itself. The protective socket is one rigid entity with the measuring arm 3, and there is a gap 16 between the measuring arm 3 and the protective socket 8 so that the measuring arm and the protective socket are not in direct contact with each other, their connection being only over the body 1.

The end of the rod-shaped measuring arm 3 is bevelled so that it presents a straight plane which is inclined at an angle of about 20° relative to the longitudinal axis of the measuring arm. The protective socket 8 has a similar shape, encircling the measuring arm, whereby the bevelled outer surface of the protective socket constitutes an abutment face 6. There is an aperture 9 in this abutment face, through which protrudes a measuring pin 4, i.e., apin attached to the bevelled tip face of the measuring arm 3. The diameter of the pin 4 is on the order of 1 mm, and it protrudes to the outside of the abutment face 6, formed by the protective socket 8, a distance of about 0.3 to 0.4 mm.

To the measuring arm 3 are attached two strain gauge transducers 5, in its central region and on its opposite sides, so that the force acting on the measuring pin 4 will cause distension of one strain gauge transducer and compression of the other. Similarly, two strain gauge transducers 2 are placed on the body 1, within the protective socket 8, one of them measuring distension and the other compression of the body when a force acts on the abutment face 6 in a way such as to bend the body 1.

Furthermore, cleaning apertures 10 and 11 have been provided in the protective socket 8 of the stiffness measuring device, one of them located in the vicinity of the tip of the protective socket 8 and the other close to the juncture between the measuring arm 3 and the body 1, in other words the apertures are located at both ends of the space 16 that is left between the measuring arm 3 and the protective socket 8. It is hereby easy to rinse, clean and disinfect through these apertures the measuring device in its entirety scrupulously by using, when necessary, a connector fitting into the aperture to squirt liquid or gas into the space between the protective socket 8 and the measuring arm 3.

The stiffness measuring device of the invention is operated as follows. The diameter of the body 1 of the measuring device is, for instance, about 6 mm, whereby it can be used in connection with arthroscopy. The abutment face 6 of the measuring device is pressed against the tissue. e.g. an articular cartilage 17, so that the abutment face 6 is flush against the surface of the articular cartilage. Hereby the measuring pin 4 extending beyond the abutment face will compress the cartilage which it meets.

Thus the articular cartilage presses against the measuring pin, and by its mediation against the measuring arm 3, with a force proportional to its stiffness. This compression produces stresses in the measuring arm 3 measurable with the transducers 5. Similar stresses are caused in the transducers 2 of the body by the act of pressing the abutment face 6 of the measuring device against the articular cartilage which is being measured.

Since the diameter of the measuring pin used in the measurement and its protrusion from the abutment face 6 both are comparatively minor, particularly as related to the thickness of the tissue that is being measured, the assumption is permissible that the effect of cartilage thickness on the result of measurement is negligible, and therefore the measured compressive force acting on the measuring pin is directly proportional to the stiffness of the cartilage.

In the foregoing the invention has been described by way of example with the aid of the enclosed drawings, while various embodiments of the invention are feasible within the scope of the inventive idea as delimited by the claims.

We claim:

1. A device for measuring the stiffness of rigid tissue, such as cartilage, the stiffness measuring device comprising:

an elongated, rigid body (1) having an abutment face (6) for pressing against the tissue that is being measured;

a measuring arm (3) rigidly attached to and located within the body and having a protruding measuring pin (4) and a first transducer (5) for sending signals measuring the force acting through the measuring pin from the tissue under measurement on the measuring arm;

the body (1) having a second transducer (2) for sending signals measuring the load acting through the abutment face of said body; and means (7) for processing the combined signals from the first and second transducers to determine the stiffness of the tissue, said body (1) comprising a protective socket (8) surrounding the measuring arm (3), the end of the socket forming the abutment face (6) comprising an aperture (9) through which the measuring pin (4) projects out beyond the outer surface of the protective socket without touching the protective socket.

2. Stiffness measuring device according to claim 1, characterized in that the first and second transducers (2,5) are strain gauges.

3. Stiffness measuring device according to claim 2, characterized in that the strain gauges are placed in pairs to constitute the first transducer and a second transducer (2,5) on opposite sides of the body (1) and of the measuring arm (3).

4. Stiffness measuring device according to claim 1 characterized in that the measuring pin (4) projects from the aperture (9) 0.1 to 1.0 mm outside the abutment face (6).

5. Stiffness measuring device according to claim 4, characterized in that the abutment face (6) is a flat surface oriented at an angle relative to the elongated body, its inclination against the longitudinal axis of the body being about 20°.

6. Stiffness measuring device according to claim 1, characterized in that the abutment face (6) is a flat surface oriented at an angle relative to the elongated body, its inclination against the longitudinal axis of the body being about 20°.

7. Stiffness measuring device according to claim 1, characterized in that the protective socket (8) comprises at least one cleaning aperture (10,11) for cleaning away any impurities that may have entered the protective socket through the aperture (9) and for disinfecting the measuring device.

8. Stiffness measuring device according to claim 1, characterized in that the aperture (9) is sealed with a resilient sealing agent which does not affect the movements of the measuring pin in relation to the protective socket.

9. A procedure for measuring the stiffness of rigid tissue, such as articular cartilage, using a device comprising an elongated body having an abutment face for pressing against the tissue being measured and a measuring arm located within the body and having a measuring pin protruding through the abutment face for pressing into the tissue without damaging the tissue, the procedure comprising the steps of:

directing a substantially planar load against the tissue through the abutment face;

directing a substantially punctiform load depressing to a constant depth against the tissue through the measuring pin;

measuring the combination of the planar load and punctiform load; and determining the stiffness of the tissue by measuring the forces counteracting the combined planar and punctiform loads.

10. A device for measuring the stiffness of rigid tissue, such as articular cartilage, the stiffness measuring device comprising:

an elongated, rigid body (1) having an abutment face (6) for pressing against the tissue that is being measured;

a measuring arm (3) rigidly attached to and located within the body (1) and comprising a protruding measuring pin (4) and a first transducer (5) for measuring the force acting through the measuring pin from the tissue under measurement on the measuring arm; and means (7) for processing the signals from the first transducer (5), said body (1) comprising a protective socket (8) surrounding the measuring arm (3), the end of the socket forming the abutment face (6) comprising an aperture (9) through which the measuring pin (4) projects out beyond the outer surface of the protective socket without touching the protective socket, the protective socket (8) including at least one cleaning aperture (10,11) for cleaning away any impurities that may have entered the protective socket through the aperture (9) and for disinfecting the measuring device.

* * * * *